United States Patent [19]

Yensen

[11] Patent Number: Plant 6,451

[45] Date of Patent: Dec. 6, 1988

[54] SALTGRASS PLANT NAMED YENSEN 3

[75] Inventor: Nicholas P. Yensen, Tucson, Ariz.

[73] Assignee: Salt Weeds, Tucson, Ariz.

[21] Appl. No.: 901,204

[22] Filed: Aug. 28, 1986

[51] Int. Cl.[4] ..... A01H 5/00

[52] U.S. Cl. ..... Plt./89

[58] Field of Search ..... Plt./89

*Primary Examiner*—Robert E. Bagwill

*Attorney, Agent, or Firm*—Cahill, Sutton & Thomas

[57] ABSTRACT

A grain variety of *Distichlis palmeri,* characterized by vigorous growth in salty soils, high pollen production and ideal height for pollenization of grain producing variety Yensen-1.

2 Drawing Sheets

DESCRIPTION

The presently described plant is related to the plant and grain described in copending applications for plant patent filed by the present inventor entitled "Yensen 1" and "Yensen 2", assigned to the present assignee, filed concurrently herewith on Aug. 29, 1986 and assigned Ser. Nos. 901,315 and 901,316, respectively.

The present invention relates to a new and distinct variety of a plant of the family Poaceae and more particularly to a plant of the species *Distichlis palmeri* (Vasey) Fassett ex I. M. Johnston, commonly known as salt grass and is a perennial herbaceous flowering plant.

The accompanying drawings comprise color photographs of my new variety of salt grass:

This new variety was discovered at test plots of Salt Weeds (an Arizona partnership) in Tucson, Ariz.

The new variety was noted in test plantings wherein approximately 100,000 seeds, seedlings and cuttings have been test planted under agricultural conditions on a total of 2.5 acres following over ten (10) years of study of salt-tolerant plants. The purpose of these large plantings was specifically to discover new varieties with crop potential and to learn their agronomic requirements. The new variety resulted from a bed seedling.

The new variety was first noted for its vigorous growth and ideal form and later for its high yield of grain on relatively long stalks. The stalks are erect and the grain heads are of a suitable height for broadcasting pollen.

The new variety is being reproduced via rhizomes in Tucson, Ariz., where a number of other varieties are also being observed.

The new variety has a number of characteristics and desirable features distinguishing it as an improved variety. These characteristics are principally the vigorous growth, high pollen production and ideal height suitable for broadcast of pollen.

The following is a detailed description of the new variety:

Parentage: A seedling from "in house" harvested caryopses (seeds) of *Distichlis palmeri.*

Propagation: To date all rhizome shoots have held true to the distinguishing characteristics of the initial shoots and it is expected that male plants from pollinated caryopses will also hold true to the distinguishing characteristics of the initial shoots as described herein.

Figure 1:
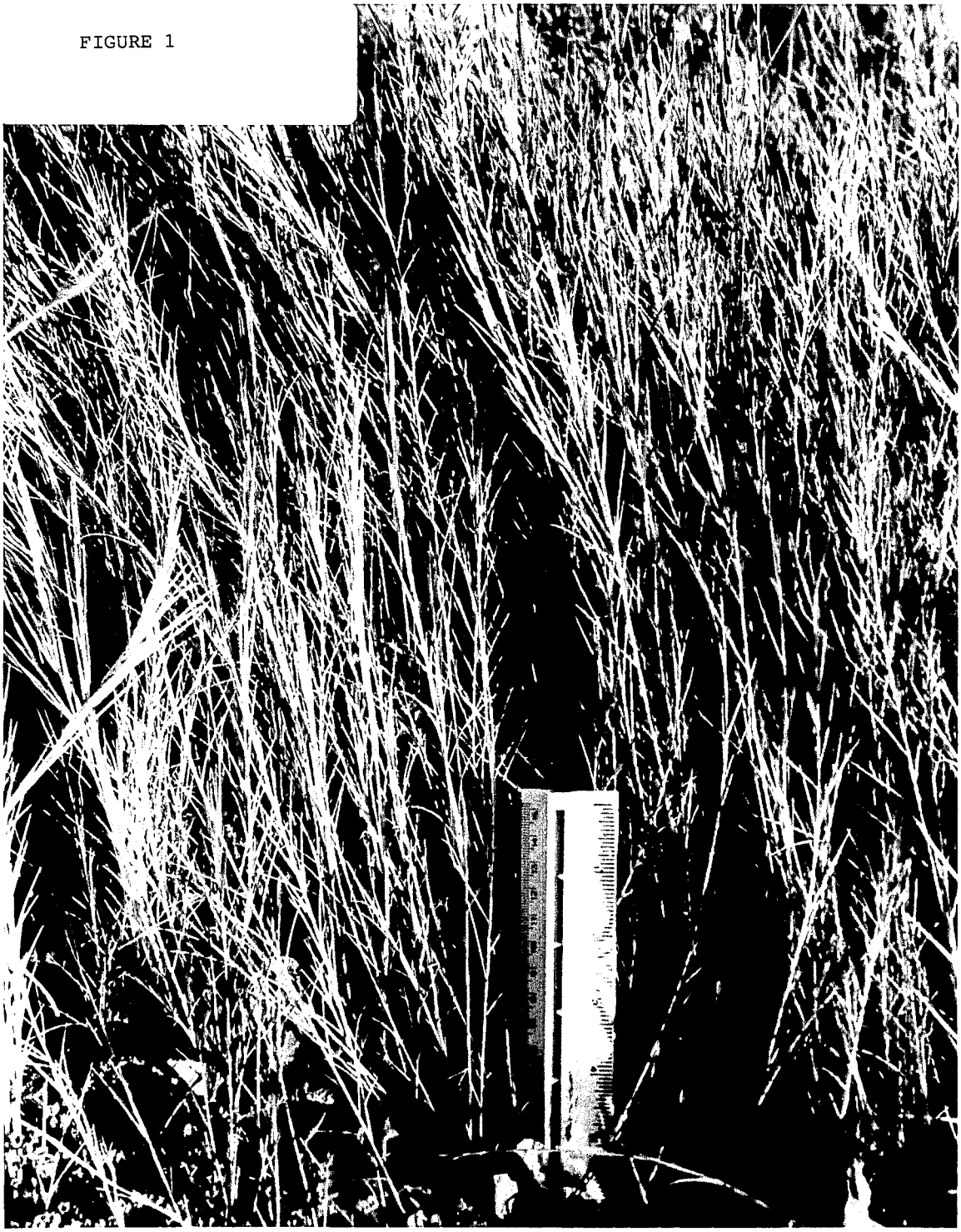
FIG. 1 is a photograph of my new salt grass.

Culms: Rigid, erect, occasionally branched, glabrous, 35–60 cm high (see FIG. 1), 2–3 mm in diameter.

Rhizomes: Thick and scaled at nodes.

Blades: Firm, rigid, ascending, pointed and pungent, involute (especially upon drying), distichous, glabrous to slightly puberulent, 3–4 mm basal width, 20–30 veins at base, typically 25–70 mm in length.

Sheath: Glabrous to slightly puberulent, with a tuft of wooly hairs at either side of the mouth, ligule smooth with pubescence apically.

Figure 2:
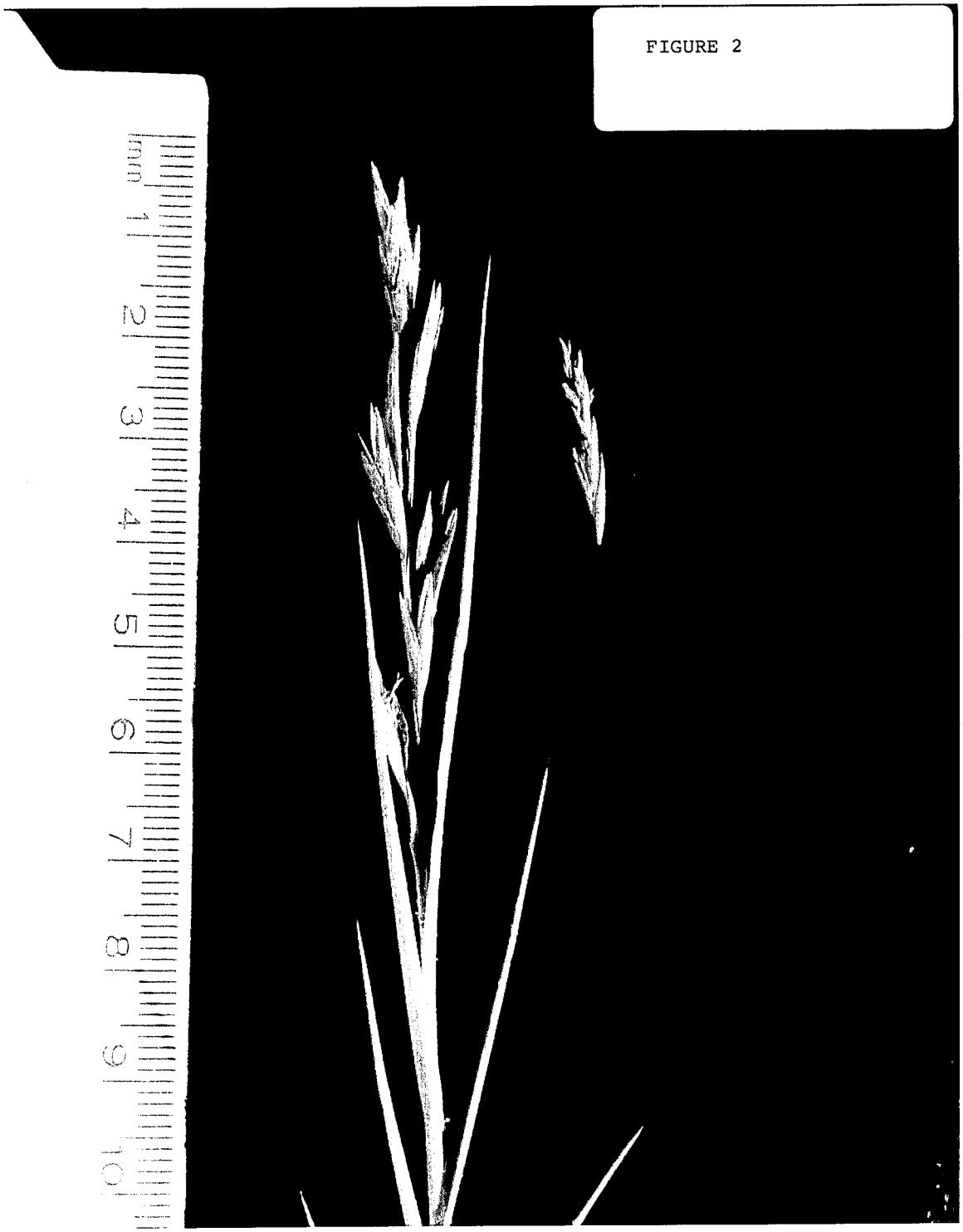
FIG. 2 is a photograph of the culm and caryopses of my new salt grass.

Inflorescence:

*Panicle.*—Erect, compoundly branched (often branched in two's), 6–10 cm in length and does not extend beyond the leaves (see FIG. 2).

*Spikelet.*—With 4–8 flowers, subtending "bracts" infertile, 10–20 mm in length, 3–4 mm in width.

*Florets.*—Lemma 6–10 mm in length decreasing slightly apically on the spikelet, 4–6 nerves on either side of a low keel. Palea 5–7 mm in length, length decreasing slightly apically on the spikelet.

*Anther.*—3–5 mm in length, length decreasing slightly apically on the spikelet, 0.5–1.0 mm in width, approximately 1 mm in height; consisting of two (2) bilobed pollen sacks with midrib extending from ca. the first $\frac{1}{4}$ to $\frac{1}{2}$ of the anther length with the remainder of the pollen sacks free, the free lobes more attenuated distally than medially; filament attached to and continuous with midrib.

*Pollen.*—20–40 microns in diameter, spherical, light yellow.

I claim:

1. A new and distinct plant variety of *Distichlis palmeri* as shown and described, which is principally characterized by vigorous growth, high pollen production and ideal height for pollination.

* * * * *